(12) United States Patent
Dequenne

(10) Patent No.: US 7,783,407 B2
(45) Date of Patent: Aug. 24, 2010

(54) METHOD AND DEVICE FOR MONITORING THE DILUTION OF THE LUBRICATING OIL BY THE FUEL IN AN INTERNAL COMBUSTION ENGINE

(75) Inventor: Bernard Dequenne, Lyons (FR)

(73) Assignees: Total Raffinage Marketing, Puteaux (FR); Delta Services Industriels S.P.R.L., Froyennes (BE)

(*) Notice: Subject to any disclaimer, the term of this patent is extended or adjusted under 35 U.S.C. 154(b) by 993 days.

(21) Appl. No.: 10/583,851

(22) PCT Filed: Dec. 17, 2004

(86) PCT No.: PCT/FR2004/003276

§ 371 (c)(1),
(2), (4) Date: Jun. 21, 2006

(87) PCT Pub. No.: WO2005/071403

PCT Pub. Date: Aug. 4, 2005

(65) Prior Publication Data

US 2007/0150161 A1    Jun. 28, 2007

(30) Foreign Application Priority Data

Dec. 23, 2003   (FR) .................................. 03 15260

(51) Int. Cl.
    *G06G 7/70*    (2006.01)
    *F01M 1/02*    (2006.01)
    *G01N 33/26*   (2006.01)
(52) U.S. Cl. .................................. 701/101; 123/196 R
(58) Field of Classification Search .................. 701/101, 701/102, 103–105; 123/196 R
See application file for complete search history.

(56) References Cited

U.S. PATENT DOCUMENTS

| 2,957,986 | A |   | 10/1960 | Quigg |       |
|-----------|---|---|---------|-------|-------|
| 4,048,497 | A |   | 9/1977  | Fritzsche |   |
| 4,321,056 | A |   | 3/1982  | Dimitroff |   |
| 5,169,785 | A | * | 12/1992 | Altman et al. ................ 436/60 |

(Continued)

FOREIGN PATENT DOCUMENTS

FR          1 500 048 A    11/1967

(Continued)

OTHER PUBLICATIONS

International Search Report for PCT/FRO4/003276 dated Aug. 9, 2004.

*Primary Examiner*—Hieu T Vo
(74) *Attorney, Agent, or Firm*—Sughrue Mion, PLLC

(57) ABSTRACT

The invention relates to a method of determining the rate of dilution of the lubricating oil by the fuel in an internal combustion engine. The invention is characterized in that it comprises the following steps consisting in: marking either the lubricating oil or the fuel with a radioactive tracer, measuring the radioactivity of an oil sample using a detector that is sensitive to the radioactive radiation emitted by the radioactive tracer, and transmitting the results of the aforementioned measurements to a computer which uses said results in order to calculate the rate of dilution of the lubricating oil by the fuel. The invention also relates to a device which is used to implement said method, in particular a test bench for engines.

28 Claims, 3 Drawing Sheets

U.S. PATENT DOCUMENTS

| | | | | |
|---|---|---|---|---|
| 5,194,910 A | * | 3/1993 | Kirkpatrick et al. | 356/70 |
| 5,445,964 A | | 8/1995 | Lee et al. | |
| 7,063,070 B2 | * | 6/2006 | Mashiki | 123/431 |
| 2006/0192122 A1 | * | 8/2006 | Chen et al. | 250/339.13 |

FOREIGN PATENT DOCUMENTS

| | | |
|---|---|---|
| GB | 1095056 A | 12/1967 |
| WO | WO 2007/147971 A2 * | 12/2007 |

* cited by examiner

METHOD AND DEVICE FOR MONITORING THE DILUTION OF THE LUBRICATING OIL BY THE FUEL IN AN INTERNAL COMBUSTION ENGINE

BACKGROUND OF THE INVENTION

The present invention relates to a method of determining the rate of dilution of the lubricating oil by the fuel of an internal combustion engine by measuring the radioactivity of a radioactive tracer introduced into the lubricating oil or the fuel, as well as a device such as a test bench for an internal combustion engine making it possible to implement this method.

For both automobile manufacturers and manufacturers of lubricating oils and/or functional additives for engine oils the importance is known of the precise knowledge of the phenomena of dilution of lubricants by the fuels within the new generation of direct injection engines, in particular those with a positive ignition or a compression ignition.

Thus, in a compression ignition engine, commonly called a diesel engine, the principle of fuel supply by direct injection within the combustion chamber is the basis for a transfer of a part of the fuel to the bottom end where it mixes with the lubricating oil.

This transfer of fuel towards the lubrication system of the engine is further accentuated for engines equipped with exhaust fume post-treatment systems, such as particle filters or catalytic converters. Indeed, in engines equipped with such post-treatment systems, additional injections of fuel can be carried out on the level of the combustion chambers at a moment when the fuel will not be burned there but sent towards the exhaust line where it will be used to regenerate the exhaust fume post-treatment system, for example for the combustion of the soot accumulated in particle filters or to modify the state of oxidation of the medium inside the catalytic system. The rate of dilution of the lubricating oil by the fuel can thus reach values of 10% by volume and more.

The introduction of fuel into the oil lubrication system has as a consequence, on the one hand, the degradation of the characteristics of the lubricant, for example a reduction of its viscosity, a dilution of the additives, and, on the other hand, an increase in the volume present within the oil pan. It results in a change in the operation of the engine which manifests itself by reduced oil pressure and abnormally high oil consumption and, in the long term, in increased wear of mechanical components, and even engine breakdown.

However, the use of exhaust fume post-treatment systems is expanding because of increasingly strict anti-pollution standards and, as a consequence, the resolution of the problem of the dilution of lubricating oil referred to above constitutes an important challenge for the automobile industry.

Automobile manufacturers must now, and in the future, perform numerous tests in developing engines exhibiting a controlled, and if possible a minimal, dilution of the lubricating oil by the fuel injected into the combustion chambers.

A certain number of techniques exist, such as packed-column or capillary gas chromatography, which make it possible to assay the quantity of fuel in oil samples taken from within an engine on a test bench. However, these analysis techniques are discontinuous, relatively complex, consume the analyzed oil sample which thus can not be reintroduced into the lubrication system and require a relatively long analysis time.

SUMMARY OF THE INVENTION

The Applicant has developed a method for evaluating the dilution of the lubricating oil by the fuel which is relatively more simple and more rapid that the known techniques, which does not consume the analyzed sample and which can function continuously, as the engine operates, so as to provide the rate of dilution of the lubricating oil by the fuel in practically real time.

This method of analysis is based on the measurement of the radioactivity of an oil sample, this radioactivity being introduced into the system in the form of a radioactive tracer present either in the lubricating oil whose dilution is to be analyzed, or in the thinner, namely the fuel feeding into the engine. Under certain conditions, this radioactivity indeed perfectly reflects the quantity of the lubricating oil or the quantity of the fuel in the oil sample analyzed and consequently makes it possible, by means of a simple calculation performed by a computer, to directly obtain the rate of dilution of the oil by the fuel.

The present invention thus has as an object a method of determining the rate of dilution of the lubricating oil by the fuel of an internal combustion engine, wherein:
- either the lubricating oil or the fuel is marked with a radioactive tracer,
- the radioactivity of an oil sample is measured, preferably continuously and as the engine operates, using a detector that is sensitive to the radioactive radiation emitted by the radioactive tracer, and
- the results of these measurements are transmitted to a computer which calculates from these results the rate of dilution of the lubricating oil by the fuel.

The invention also has as an object a device that makes it possible to implement such a method of analysis, in particular a test bench for an internal combustion engine, comprising:
- an internal combustion engine, lubricated by a lubricating oil and supplied with an air/fuel mixture, with either the lubricating oil or the fuel containing a radioactive tracer,
- a means allowing the temporary sampling and the re-injection, continuously or discontinuously, of an oil sample from the oil system of the engine,
- a detector, sensitive to the radioactive radiation emitted by the radioactive tracer present in the oil sample, which is in the immediate vicinity of this means of temporary sampling and re-injection, and
- connected to said detector, a computer programmed to calculate, from the results provided by said detector of the measurements of the radioactivity of the oil sample, the rate of dilution of the lubricating oil by the fuel.

DETAILED DESCRIPTION OF THE NON-LIMITING EMBODIMENTS OF THE INVENTION

Figure 1:
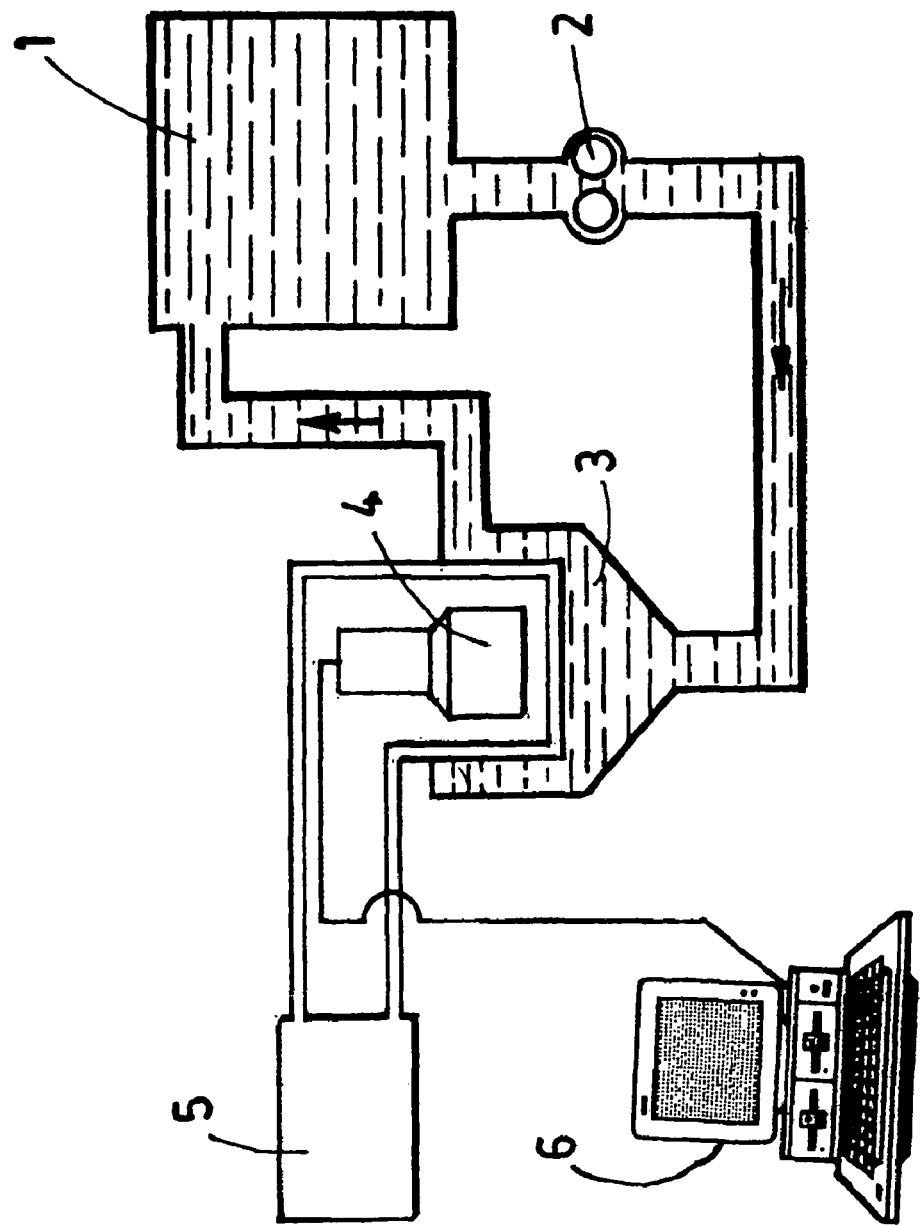
FIG. 1 depicts components in a system for determining a rate of dilution of a lubricating oil.

To describe the method and the device of the present invention in more detail, the terms "lubricating oil" and "lubricant" will be used below in a perfectly equivalent way to indicate the non-diluted oil or the fraction of oil in the oil/fuel mixture which is to be analyzed. Additionally, the term "oil sample" is used systematically to indicate the sample deviated or taken temporarily for which the radioactivity is measured. At the beginning of the engine test, this "oil sample" is of course exclusively made up of the lubricant and does not yet contain fuel.

It should be noted in addition that the term "lubricating oil" or its equivalent indicates the final lubricating product, that is to say, the lubricant base containing all of the functional additives possibly present and possibly the radioactive tracer which, as will be seen below, can be one of these functional additives.

The method for determining the rate of dilution of the lubricating oil by the fuel in an engine cannot be implemented with just any radioactive tracer. In particular, it must meet the conditions described in the paragraphs below.

The radioactive tracer must not disturb the operation of the engine or modify in an undesirable way the physico-chemical properties of the lubricating oil or the fuel. To this end, it must be in particular either chemically inert with respect to the other components of the lubricating oil or the fuel, or have a function similar to that of one of their components (for example a functional additive) and to partially or completely replace said component.

The radioactive tracer must have sufficient radioactivity to allow precise and reproducible measurements. The choice of the radioactive tracer is related in particular to the quantity of the oil sample taken and to the sensitivity of the detector used. In other words, if the detector is not very sensitive the radioactivity of the oil sample must be high (high radioactivity of the radioactive tracer or a high concentration of a radioactively relatively weak radioactive tracer). On the other hand, if the detector used is highly sensitive, the radioactivity of the oil sample can be relatively lower.

Lastly, the radioactive tracer must be selected in a manner in which its quantity in circulation in the oil system of the engine is, throughout the duration of the process, directly proportional either to the quantity of the lubricating oil or to the quantity of the fuel in circulation in the oil system of the engine.

This proportionality depends on the physico-chemical properties of the radioactive tracer and of the liquid medium (lubricating oil or fuel) in which it is initially introduced. Indeed, to reflect the quantity of the lubricating oil or the quantity of the fuel in the oil sample (oil/fuel mixture) at any moment, the radioactive tracer must neither accumulate in the mixture when the oil or the fuel is consumed, nor be consumed more quickly than the oil or the fuel, for example by evaporation, combustion or thermal decomposition, nor be trapped somewhere in the engine, such as in the oil filter.

In light of the above, those skilled in the art will choose the radioactive tracer so that its physico-chemical properties (volatility, thermal stability, chemical reactivity) match those of the liquid medium in which it is introduced and for which it must reflect the quantity. In particular, those skilled in the art will be able to find a tracer suitable for a given medium by subjecting a tracer/lubricating oil mixture or a tracer/fuel mixture to the temperature and pressure conditions that exist in an engine.

As explained above, the method of the present invention can be implemented in principle either with a fuel marked with a radioactive tracer or with a marked lubricating oil.

The use of a radioactive fuel implies the marking of a relatively large volume of the aforesaid fuel and the control of the discharge, in the exhaust fumes, of the products of combustion of the fuel that includes the radioactive tracer.

In the case of the use of a radioactive lubricant, the volume is lower and the possible discharges in the exhaust fumes are very limited and are dependent on the consumption of oil.

In the following description, the method of the invention is explained in further detail for the embodiment in which the lubricating oil contains the radioactive tracer initially introduced.

The usable detectors are the probes for detecting ionizing radiation (beta, X or gamma rays) which can be either a scintillation counter of a liquid or solid type (sodium iodide crystals NaI(T1), BGO crystals), or of a semiconductor type (germanium crystals, CZT crystals). It should be noted in addition that the detector can simultaneously detect the presence of various radioactive tracers. When the radioactivity of the oil sample is high (high radioactivity of the radioactive tracer or a high concentration of a radioactive tracer of weak radioactivity), the detector does not need to be highly sensitivity. On the other hand, when the radioactivity of the oil sample is not high, the detector will require a higher sensitivity. Preferentially, and in order to limit the quantity of the radioactive tracers used, a measurement probe with a higher detection efficiency, for example a 3×3 inches sodium iodide type crystal, will be used.

This type of detector can exist in a compact form allowing for the possibility of a device on board the vehicle.

In general, it is necessary to convey an oil sample from the oil system of the engine to be tested towards a fixed-volume measurement chamber located in or near the detector. This "temporary sampling" followed by the reintroduction of this sample into the oil system is preferably achieved by a diversion. For practical reasons relating to the regulation of the engine, this diversion is preferably located in an area of the oil system characterized by low, or no, oil pressure.

The signals detected by the detector are then processed by a series of means making it possible to calculate the rate of dilution of the lubricating oil by the fuel. These means comprise in particular a means of processing the signal detected (for example an amplifier, a filter and an analog/numerical ADC converter), a means of processing impulses (for example a multi-channel analyzer) and a means of storing and processing collected data, for example a personal computer. For the calculation of the rate of dilution, the computer program must of course take into account the natural decrease in the radioactivity of the radioactive tracer, which is directly related to its half-life.

The deviation of the oil sample, the measuring of the radioactivity of the sample deviated and the processing of the results are preferably performed continuously on a heat engine under operation.

The radioactive tracer usable in the present invention can be either an organic or mineral compound of a radioactive element (radionuclide) or the radioactive element itself which is then in elemental form. However, taking into account the considerations above concerning the physico-chemical properties of the radioactive tracer with respect to those of the lubricating oil, the molecular, organic or mineral forms of radioactive tracers, in particular the organic form, are preferred compared to the elemental forms of radionuclides.

The radioactive tracer is thus selected among the organic or mineral compounds or the elements that meet the conditions indicated above (i.e., inert character with respect to the lubricant or substitution for the one of the components of the lubricant, sufficient radioactivity and oil/tracer proportionality). However, for obvious reasons related to handling and to environmental protection, tracers containing radionuclides possessing a short half-life, preferably a half-life less than 3 years, in particular less than 1 year and even more preferentially less than 30 days, will be chosen by preference. In this manner, the production of radioactive waste with a long half-life will be avoided.

It is preferable that the half-life of the radionuclide is equal to or greater than the anticipated duration of the test. The computer, by means of the law of radioactive decay, will be able to easily correct the measured value.

The following can be cited as examples of radionuclides having a suitable half-life (indicated between parentheses): $^{22}$Na (2.61 years), $^{65}$Zn (243.8 days), $^{45}$Ca (165 days), $^{35}$S (87.2 days), $^{32}$P (14.3 days), $^{47}$Ca (4.54 days), $^{99}$Mo (65.9 hours), $^{82}$Br (35.3 hours), $^{64}$Cu (12.7 hours), $^{99m}$Tc (6.01 hours), $^{28}$Mg (20.91 hours), $^{68}$Ge (270.95 days), $^{69}$Ge (39 hours), $^{77}$Ge (11.30 hours), $^{85}$Sr (64.8 days) and $^{56}$Co (77.3 days).

These radioactive tracers are in general produced artificially by nuclear reactions, in particular by activation reactions. This activation is performed according to methods familiar to those skilled in the art, for example by exposing the inactive elements or compounds containing the aforesaid inactive elements to a source of neutron radiation, or by exposure to a beam of accelerated ions arising from a particle accelerator.

Depending on the case, the inactive elements or compounds containing the aforesaid inactive elements are activated either before their incorporation in the lubricating oil or the fuel, or within the oil or the fuel, that is to say, by exposing the oil or the fuel containing the element or the compound to be activated to neutron radiation or to a proton beam, for example.

One of the possible options for obtaining artificial radionuclides is to incorporate the inactive elements or the compounds containing the aforesaid inactive elements in a suitable quantity of a vector (for example a solvent or a thinner such as an oil), then to subject this mixture to activation and finally to add it to the lubricating oil or to the fuel.

The radioactive tracers can be additives typically used in lubricating oils or in fuels, such as anti-corrosion agents, antioxidants, agents that modify viscosity, lubricating additives, dyes, additives that lower the pour point, and detergent or dispersing additives. The following can be cited as examples of such radioactive tracers that function as functional additives: zinc dithiophosphate, the calcium or magnesium sulfonates such as the alkylsulfonates, the arylsulfonates or the calcium or magnesium alkylarylsulfonates, the calcium phenolates, the magnesium phenolates, the calcium salicylates and the magnesium salicylates.

However, the use of radioactive tracers which have no physical or chemical function in the engine lubrication system is quite suitable as well.

The Applicant has noted that the radioactive tracers particularly interesting for introduction into the lubricating oil are certain compounds of germanium-69. These compounds are selected, for example, among the tetra-alkyl germaniums. As the boiling point of these tetra-alkyl germaniums is proportional to the length of the alkyl chains, a mixture of tetra-alkyl germaniums will be used that advantageously possesses alkyl chains of such length that the boiling point of the mixture falls within the distillation range of the oil used. As examples, tetra-hexyl germanium, tetra-heptyl germanium and tetra-octyl germanium each have a boiling point comparable to that of a traditional engine lubricant.

EXAMPLE 1

Continuous Monitoring of the Rate of Dilution of a Lubricating Oil by Diesel Oil in a Closed Oil System FIG. 1 illustrates the experimental device used to carry out the method described in this example. Using a pump (2) whose flow rate is 3 liters/minute, a volume of 5.5 liters of a 15W40 mineral type lubricating oil (TOTAL brand) is made to circulate in a closed system. Said oil contains a radioactive tracer. The tracer used in this example is $^{99m}$Tc in the form of sodium pertechnetate (Na$^{99m}$TcO$_4$) in an aqueous solution. The characteristics of this radioactive tracer are as follows: gamma emission at 140 keV, emission intensity of 89% and a half-life of 6 hours. In order to facilitate the incorporation of the aqueous solution in the lubricating oil, a water dispersant sold under the brand name "Bardahl Water Dispersant" is used.

The closed system comprises, in a series, a temperature-adjustable oil reservoir (1) that simulates the casing of the internal combustion engine and a double-walled cylinder (3) with a capacity of 1 liter that constitutes the analysis chamber, this volume being that of the oil sample taken. The temperature of the oil is maintained at 70° C. Placed in the center of the analysis chamber is a standard sodium iodide NaI(T1) detector (4), 7.62×7.62 cm (3×3 inches) in size, with an integrated photomultiplier, whose temperature is stabilized at 30° C. by a thermostatic group (5). The detector, which is sensitive to the 140 keV gamma radiation emitted by the radioactive tracer, is connected to a data acquisition and processing system (6) comprised of a Canberra model 2007P preamplifier, a Canberra model 2020 spectroscopy amplifier, a Canberra model 8087 ADC converter and a Canberra model S100 multi-channel card. The software used in this example goes by the name "IDSWear" and is sold by Atlantic Nuclear Services (ANS), which is based in Canada. This software makes it possible to follow the temporal progress of the counting rate of the detector in a window of energy extending from 100 keV to 180 keV in which the signal characteristic of $^{99m}$Tc is located.

By marking the 5.5 liters of lubricating oil with 1 MBq of $^{99m}$Tc, the initial counting rate recorded for the undiluted oil is 9020 counts/second, which corresponds to the activity of the liter of oil contained in the analysis chamber. After 50 minutes, 95 minutes and 120 minutes, respectively, 55 ml of fuel, 200 ml of fuel and 200 ml of fuel (diesel oil, European standard) are added into the oil reservoir, which corresponds to a dilution of 0.99% by volume, 4.4% by volume and 7.6% by volume, respectively.

Figure 2:
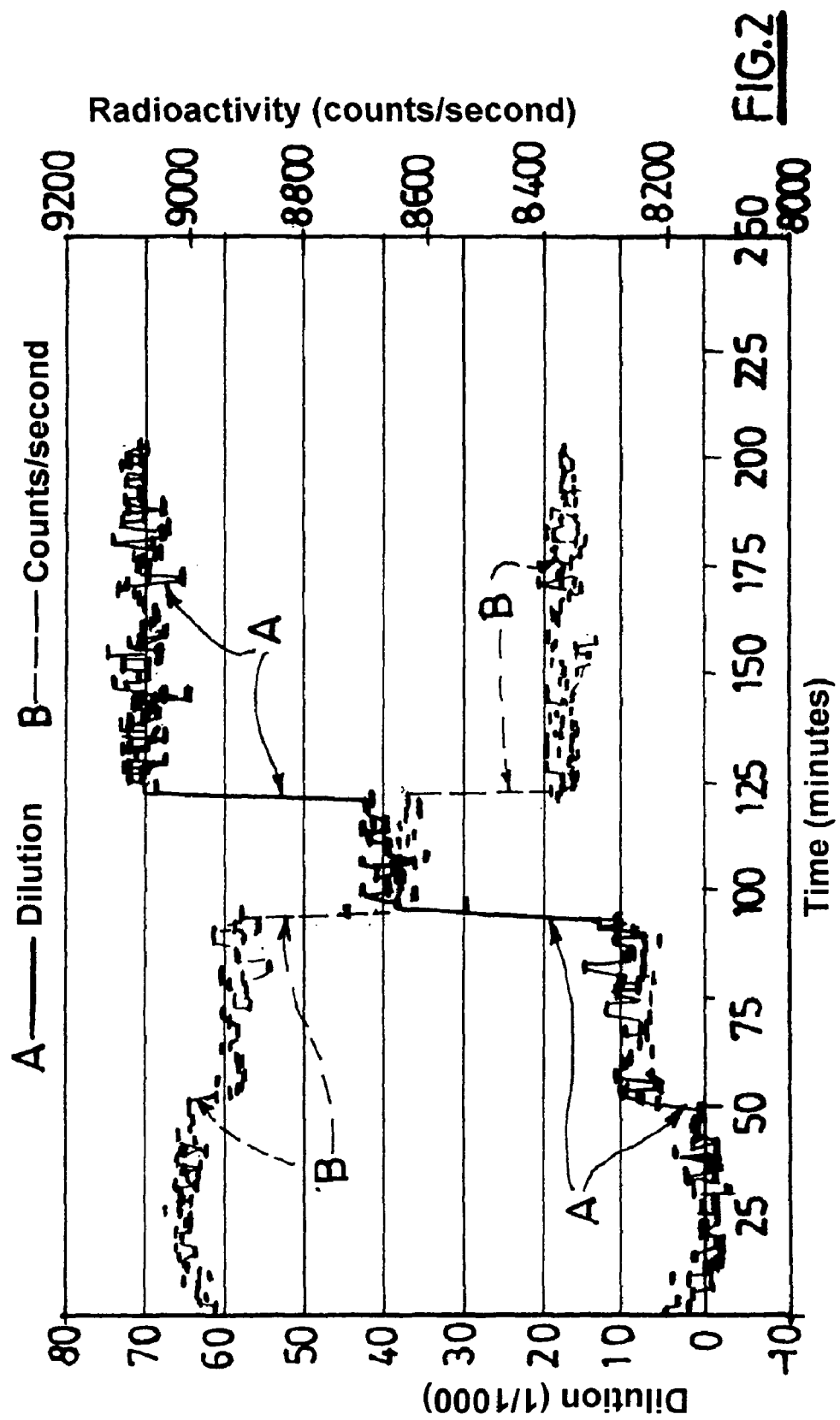
FIG. 2 is a graph showing progress of the counting rate at the level of the analysis chamber as a function of time and the dilution of the lubricating oil by the diesel oil in an oil/diesel oil mixture.

FIG. 2 shows, together, the progress as a function of time of the counting rate at the level of the analysis chamber (light-gray dots) and of the dilution of the lubricating oil by the diesel oil in the oil/diesel oil mixture (black dots). The dilution curve is calculated, by the software, from the measured values of the counting rate, following a proportionality rule: the initial counting rate corresponds to a dilution of 0% by volume whereas a zero counting rate corresponds to a dilution of 100% by volume.

This example shows that the counting rate measured by the detector correctly reflects the rate of dilution imposed by the addition of the fuel (diesel oil), within the limits of measurement uncertainties.

EXAMPLE 2

Continuous Monitoring of the Rate of Dilution of a Lubricating Oil by Diesel Oil in a Diesel Engine In this example, a diesel engine test bench is equipped with a low flow-rate oil diversion system. This system makes it possible to continuously sample lubricant coming from the oil pan towards the detector before it is returned to the engine. The experimental device is practically identical to that of Example 1 except that the oil reservoir is replaced by a diesel engine. For this test, the diesel engine was operated in typical fashion with a low load and at a low speed in order to favor dilution by the diesel oil: 1500 rpm, 8.2 kW of power and an oil temperature of 80° C.

The tracer used in this example is germanium-69 (Ge-69) in the form of an organic compound, soluble in oil, with a boiling point in the middle of the distillation range of the oil (at approximately 450° C.). The tracer is used at a concentration of 1 MBq in 5 liters of oil. The characteristics of this radioactive tracer are as follows:

gamma emissions at 511 keV (47%), 574 keV (13%), 871 keV (12%), 1106 keV (36%) and 1336 keV (5%),
a half-life of 39 hours.

The initial counting rate recorded for the undiluted oil is approximately 950 counts/second. This counting rate is accompanied by a statistical error at each measurement point on the order of 0.6%.

The engine used in this example is a 4-cylinder common rail direct injection diesel engine.

In parallel with the continuous measurements, small samples of lubricant are taken at regular intervals and the rate of dilution of the oil by the diesel oil is determined by the traditional gas-phase chromatography method (DIN 51380 standard).

Figure 3:
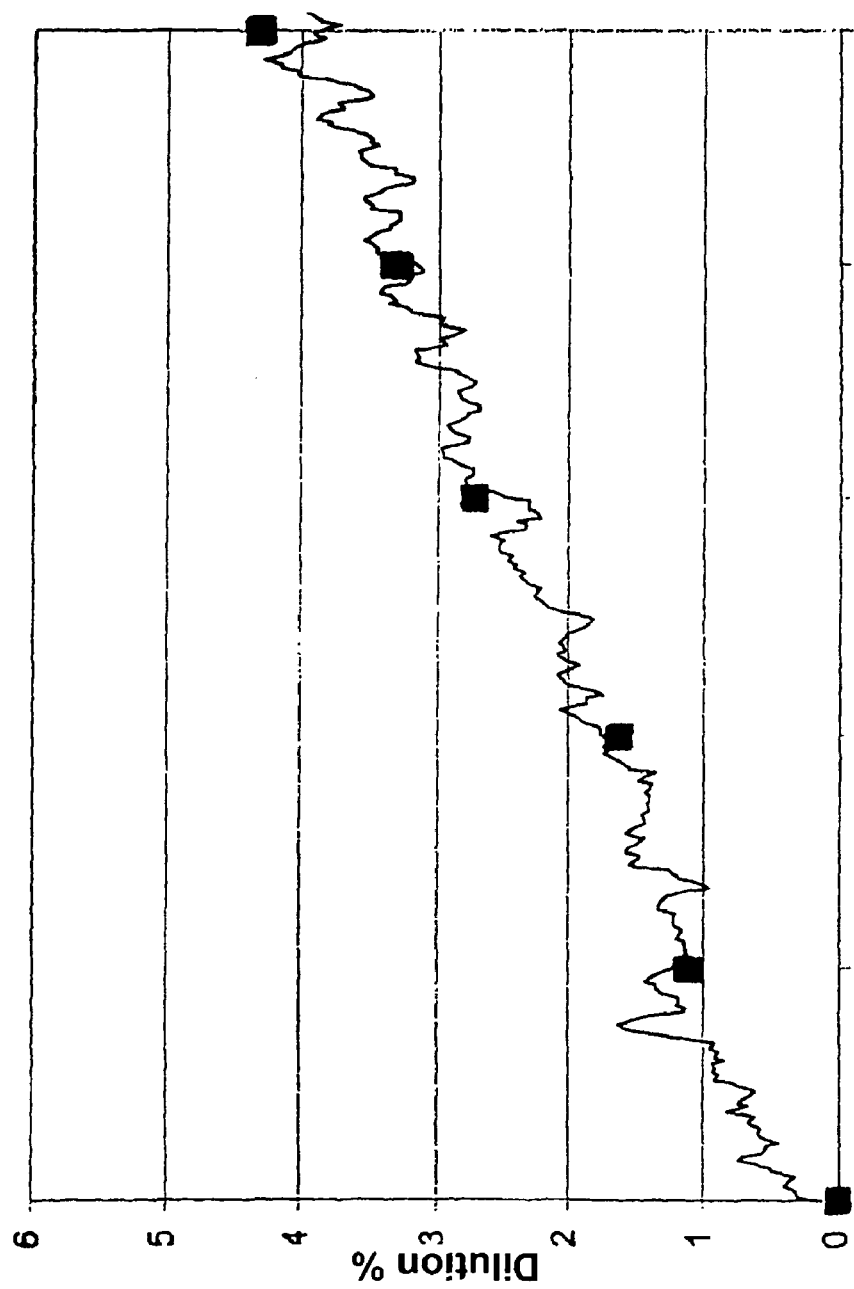
FIG. 3 is a graph showing the progress of the rate of dilution of the oil by the diesel oil.

The curve in FIG. 3 shows the progress of the rate of dilution (expressed in %) of the oil by the diesel oil, measured continuously in the oil pan by the radioactive tracer detection system (continuous line) and measured at regular intervals by gas-phase chromatography (filled squares). It can be noted that the continuous measurement of the rate of dilution according to the method of the invention perfectly matches the discontinuous determination method of the current state of the art.

The invention claimed is:

1. A system for monitoring a rate of dilution of a lubricating oil by fuel of an internal combustion engine, the internal combustion engine being lubricated by a lubricating oil and supplied with an air/fuel mixture, with either the lubricating oil or the fuel containing a radioactive tracer, the system comprising:
means for temporarily sampling and then re-injecting, continuously or discontinuously, an oil sample from an oil system of the internal combustion engine,
a detector, sensitive to radioactive radiation emitted by the radioactive tracer present in the oil sample and operable to measure the emitted radioactive radiation, is provided adjacent to the means for temporary sampling and re-injection of the oil sample, and
a computer, connected to the detector, is programmed to calculate, from measurement results provided by the detector, the rate of dilution of the lubricating oil by the fuel.

2. The system according to claim 1, wherein the lubricating oil contains the radioactive tracer.

3. The system according to claim 1, wherein the fuel contains the radioactive tracer.

4. The system according to claim 1,
wherein the means for temporary sampling and re-injection of the oil sample is a deviation.

5. The device system according to claim 1, wherein the means for temporary sampling and re-injection of the oil sample samples and re-injects the oil sample in an area of the oil system of the engine which is under no or low oil pressure.

6. The system according to claim 1, wherein
the radioactive tracer is an organic or mineral compound of a radioactive element.

7. The system according to claim 6, wherein the radioactive element has a half-life of less than 3 years.

8. The system according to claim 7, wherein the radioactive element is selected the group consisting of $^{22}$Na, $^{65}$Zn, $^{45}$Ca, $^{35}$S, $^{32}$P, $^{47}$Ca, $^{99}$MO, $^{82}$Br, $^{64}$Cu, $^{99m}$TC, $^{28}$Mg, $^{68}$Ge, $^{69}$Ge, $^{77}$Ge, $^{85}$Sr and $^{56}$CO.

9. The system according to claim 8, wherein the radioactive tracer is selected from tetra-alkyl germaniums containing $^{69}$Ge.

10. The system according to claim 8, wherein the radioactive tracer is selected from the group consisting of tetra-hexyl germaniums, tetra-heptyl germaniums and tetra-octyl germaniums or a mixture thereof.

11. The system according to claim 6, wherein the radioactive element has a half-life of less than 1 year.

12. The system according to claim 6, wherein the radioactive element has a half-life of less than 30 days.

13. The system according to claim 1, wherein the detector is an ionizing radiation detection probe.

14. The system according to claim 1, wherein the radioactive tracer is an organic compound of a radioactive element.

15. A method of determining a rate of dilution of a lubricating oil by fuel of an internal combustion engine, where either the lubricating oil or the fuel is marked with a radioactive tracer, the method comprising:
measuring radioactivity of an oil sample using a detector that is sensitive to radioactive radiation emitted by the radioactive tracer,
transmitting results of the measurements to a computer, and
the computer calculating the rate of dilution of the lubricating oil by the fuel based on the results.

16. The method according to claim 15, wherein the lubricating oil contains the radioactive tracer.

17. The method according to claim 15, wherein the fuel contains the radioactive tracer.

18. The method according to claim 15, wherein the oil sample for which the radioactivity is measured is conveyed towards the detector and then re-injected into an oil system of the internal combustion engine by a deviation.

19. The method according to claim 18, wherein the deviation takes the oil sample from an area of the oil system of the engine which is under no or low oil pressure.

20. The method according to claim 15, wherein the radioactive tracer is an organic or mineral compound of a radioactive element.

21. The method according to claim 20, wherein the radioactive element has a half-life of less than 3 years.

22. The method according to claim 21, wherein the radioactive element is selected the group consisting of $^{22}$NA, $^{65}$Zn, $^{45}$Ca, $^{35}$S, $^{32}$P, $^{47}$Ca, $^{99}$MO, $^{82}$Br, $^{64}$Cu, $^{99m}$Tc, $^{28}$Mg, $^{68}$Ge, $^{69}$Ge, $^{77}$Ge, $^{85}$Sr and $^{56}$CO.

23. The method according to claim 22, wherein the radioactive tracer is selected from tetra-alkyl germaniums containing $^{69}$Ge.

24. The method according to claim 22, wherein the radioactive tracer is selected from the group consisting of tetra-hexyl germaniums, tetra-heptyl germaniums and tetra-octyl germaniums or a mixture thereof.

25. The method according to claim 20, wherein the radioactive element has a half-life of less than 1 year.

26. The method according to claim 20, wherein the radioactive element has a half-life of less than 30 days.

27. The method according to claim 15, wherein the detector is an ionizing radiation detection probe.

28. The method according to claim 15, wherein the radioactive tracer is an organic compound of a radioactive element.

* * * * *